US011213426B2

(12) United States Patent
Cook et al.

(10) Patent No.: US 11,213,426 B2
(45) Date of Patent: Jan. 4, 2022

(54) THERMALLY ROBUST MULTI-SPOT LASER PROBE

(71) Applicant: NOVARTIS AG, Basel (CH)

(72) Inventors: Christopher Cook, Laguna Niguel, CA (US); Alireza Mirsepassi, Irvine, CA (US)

(73) Assignee: Alcon Inc., Fribourg (CH)

( * ) Notice: Subject to any disclaimer, the term of this patent is extended or adjusted under 35 U.S.C. 154(b) by 319 days.

(21) Appl. No.: 16/217,368

(22) Filed: Dec. 12, 2018

(65) Prior Publication Data

US 2019/0175404 A1 Jun. 13, 2019

Related U.S. Application Data

(60) Provisional application No. 62/622,299, filed on Jan. 26, 2018, provisional application No. 62/597,550, filed on Dec. 12, 2017, provisional application No. 62/598,653, filed on Dec. 14, 2018.

(51) Int. Cl.
| | | |
|---|---|---|
| *A61F 9/008* | (2006.01) | |
| *A61B 18/22* | (2006.01) | |
| *G02B 27/10* | (2006.01) | |
| *G02B 6/032* | (2006.01) | |

(52) U.S. Cl.
CPC .......... *A61F 9/00821* (2013.01); *A61B 18/22* (2013.01); *G02B 6/032* (2013.01); *G02B 27/106* (2013.01); *G02B 27/1093* (2013.01); *A61F 2009/00863* (2013.01)

(58) Field of Classification Search
CPC ....... A61F 9/00821; A61F 2009/00863; A61B 18/22; G02B 6/032; G02B 27/106; G02B 27/1093

USPC ............................................................ 606/4
See application file for complete search history.

(56) References Cited

U.S. PATENT DOCUMENTS

| | | | |
|---|---|---|---|
| 5,199,431 A | 4/1993 | Kittrell | |
| 5,496,305 A | 3/1996 | Kittrell | |
| 5,625,638 A | 4/1997 | Trost | |
| 5,693,043 A | 12/1997 | Kittrell | |
| 5,921,981 A * | 7/1999 | Bahmanyar ............ | A61B 3/135 606/4 |
| 6,066,128 A | 5/2000 | Bahmanyar et al. | |
| 6,096,028 A | 8/2000 | Bahmanyar et al. | |
| 6,893,432 B2 | 5/2005 | Intintoli et al. | |
| 7,189,226 B2 | 3/2007 | Auld et al. | |
| 7,302,142 B2 | 11/2007 | Conde | |

(Continued)

FOREIGN PATENT DOCUMENTS

| | | |
|---|---|---|
| JP | A1994014936 A | 1/1994 |
| JP | 2013048864 A | 3/2013 |

(Continued)

*Primary Examiner* — Aaron F Roane

(57) ABSTRACT

A laser probe includes a cannula, at least one optical fiber positioned within the cannula, and a lens positioned within the cannula at a distal end of the fiber. The lens is adapted to receive a laser beam from the optical fiber at a proximal end of the lens and to transmit the laser beam towards a distal end of the lens. The laser probe includes an optical element configured coupled to the cannula by a brazed joint and to receive the laser beam from the distal end of the lens and emit the laser beam from the probe. The brazed joint may form a hermetic or liquid-tight seal between the optical element and the cannula.

19 Claims, 2 Drawing Sheets

(56) References Cited

U.S. PATENT DOCUMENTS

| | | |
|---|---|---|
| 7,448,995 B2 | 11/2008 | Wiklof |
| 7,566,173 B2 | 7/2009 | Auld et al. |
| 8,398,240 B2 | 3/2013 | Smith |
| 8,488,930 B2 | 7/2013 | Papac |
| 8,498,506 B2 | 7/2013 | Smith |
| 8,561,280 B2 | 10/2013 | Diao et al. |
| 8,571,364 B2 | 10/2013 | Smith |
| 8,764,261 B2 | 7/2014 | Smith |
| 8,903,475 B2 | 12/2014 | Brennan et al. |
| 8,939,964 B2 | 1/2015 | Smith |
| 8,951,244 B2 | 2/2015 | Smith |
| 8,968,347 B2 | 3/2015 | McCollam |
| 9,055,885 B2 | 6/2015 | Horvath |
| 9,107,730 B2 | 8/2015 | Huculak et al. |
| 9,211,214 B2 | 12/2015 | Rubinchik |
| 9,308,128 B2 | 4/2016 | Smith |
| 9,364,982 B2 | 6/2016 | Schaller |
| 9,387,040 B2 | 7/2016 | Smith |
| 9,402,643 B2 | 8/2016 | Auld |
| 9,603,741 B2 * | 3/2017 | Berlin .................. A61F 9/00802 |
| 9,681,793 B2 | 6/2017 | Artsyukhovich |
| 10,012,800 B2 | 7/2018 | Diao |
| 10,016,302 B2 | 7/2018 | Shazly |
| 10,111,778 B2 | 10/2018 | Smith |
| 10,245,181 B2 | 4/2019 | Diao |
| 10,433,718 B2 | 10/2019 | Liolios |
| 10,441,157 B2 | 10/2019 | Smith |
| 2002/0045811 A1 | 4/2002 | Kittrell |
| 2004/0236183 A1 | 11/2004 | Durell |
| 2005/0256377 A1 * | 11/2005 | Deppmeier ........ A61B 1/00165 600/176 |
| 2006/0184162 A1 | 8/2006 | Smith |
| 2008/0051770 A1 | 2/2008 | Scheller et al. |
| 2008/0177257 A1 | 7/2008 | Smith et al. |
| 2008/0215041 A1 | 9/2008 | Zemmouri |
| 2008/0243108 A1 | 10/2008 | Murakami |
| 2009/0270850 A1 | 10/2009 | Zhou |
| 2009/0287196 A1 | 11/2009 | Zelickson |
| 2009/0287197 A1 | 11/2009 | Hanley |
| 2010/0027943 A1 | 2/2010 | Armani |
| 2010/0261961 A1 | 10/2010 | Scott |
| 2011/0122366 A1 | 5/2011 | Smith |
| 2011/0144627 A1 | 6/2011 | Smith |
| 2012/0191078 A1 | 7/2012 | Yadlowsky |
| 2013/0150839 A1 | 6/2013 | Smith |
| 2014/0180264 A1 | 6/2014 | Diao et al. |
| 2014/0194862 A1 | 7/2014 | Smith et al. |
| 2014/0200566 A1 | 7/2014 | Smith |
| 2014/0250668 A1 | 9/2014 | Smith |
| 2015/0351629 A1 | 12/2015 | Wheatley |
| 2015/0366432 A1 | 12/2015 | Artsyukhovich |
| 2016/0178844 A1 | 6/2016 | Griffin |
| 2018/0055596 A1 | 3/2018 | Johnson |
| 2018/0243136 A1 | 8/2018 | Diao |
| 2018/0243137 A1 | 8/2018 | Diao |
| 2018/0333304 A1 | 11/2018 | Diao |
| 2018/0344528 A1 | 12/2018 | Farley |
| 2019/0142544 A1 | 5/2019 | Horn |
| 2019/0175217 A1 | 6/2019 | Cook |
| 2019/0175273 A1 | 6/2019 | Cook |
| 2019/0175300 A1 | 6/2019 | Horn |
| 2019/0175405 A1 | 6/2019 | Diao et al. |
| 2019/0175406 A1 | 6/2019 | Cook |
| 2019/0175407 A1 | 6/2019 | Bacher |
| 2019/0175408 A1 | 6/2019 | Diao |
| 2019/0209372 A1 | 7/2019 | Farley |
| 2019/0307527 A1 | 10/2019 | Grueebler |
| 2019/0365569 A1 | 12/2019 | Skovgaard |
| 2020/0107960 A1 | 4/2020 | Bacher et al. |

FOREIGN PATENT DOCUMENTS

| | | | |
|---|---|---|---|
| WO | WO9208429 | A1 | 5/1992 |
| WO | WO9208427 | A2 | 9/1992 |
| WO | WO2001037769 | A1 | 5/2001 |
| WO | WO2008024848 | A2 | 2/2008 |
| WO | WO2018113887 | A2 | 6/2018 |

* cited by examiner

THERMALLY ROBUST MULTI-SPOT LASER PROBE

PRIORITY CLAIM

This application claims the benefit of priority of U.S. Provisional Patent Application Ser. No. 62/622,299 titled "THERMALLY ROBUST MULTI-SPOT LASER PROBE," filed on Jan. 26, 2018, whose inventors are Alireza Mirsepassi, and Christopher Cook, which is hereby incorporated by reference in its entirety as though fully and completely set forth herein.

FIELD

The present disclosure relates to laser probes useful in medical procedures, including ophthalmology.

BACKGROUND

Laser photocoagulation therapy addresses ocular conditions such as retinal detachments and tears as well as proliferative retinopathy resulting from diseases such as diabetes. The abnormally high blood sugar in a diabetic stimulates the retinal vessels to release growth factors that in turn encourage an undesirable proliferation of blood vessels and capillaries over the retinal surface. These proliferated blood vessels are very delicate and will readily bleed into the vitreous. The body responds to the damaged vessels by producing scar tissue, which may then cause the retina to detach so as to eventually cause blindness.

In laser pan retinal photocoagulation, a laser probe is used to burn spots across the retina. The number of required laser photocoagulations for any one treatment of the retina may be large—1,000 to 1,500 spots are commonly burned. Accordingly, multi-spot laser probes capable of delivering a plurality of photocoagulation beams simultaneously enable the burning of multiple spots at a time and may be used to expedite a photocoagulation procedure. Multi-spot laser probes can be generally classified into two categories: "multi-spot/multi-fiber" laser probes which produce multiple laser beams through a corresponding array of optical fibers, and "multi-spot/single-fiber" laser probes which use a single fiber.

To create a single burn spot on the retina, the laser power requirement is approximately 250-500 mW. To produce multiple burn spots in parallel, multi-spot laser probes must deliver corresponding multiples of this requisite power. For instance, multi-spot probes capable of producing four burn spots simultaneously may generate anywhere from 1 W to 3 W through a confined space at the probe tip. In some surgical use cases, such as in the case of bleeding and occlusion at the probe tip, significant light absorption at the tip may occur, causing thermal-induced failure of the probe. Accordingly, there is a need for an improved multi-spot laser probe which is thermally robust and resistant to meltdown.

SUMMARY

Certain embodiments include a laser probe having a cannula, at least one optical fiber positioned within the cannula, and a lens positioned within the cannula at a distal end of the fiber. The lens is adapted to receive a laser beam from the optical fiber at a proximal end of the lens and to transmit the laser beam towards a distal end of the lens. The laser probe also includes an optical element configured to receive the laser beam from the distal end of the lens and emit the laser beam from the probe. The optical element is coupled to the cannula by a brazed joint. The brazed joint may form a hermetic or liquid-tight seal between the optical element and the cannula.

In certain embodiments the brazed joint comprises a first inter-molecular bond between a braze filler and an outer surface of the optical element, and a second inter-molecular bond between the braze filler and an inner surface of the cannula. Some variants include a first inter-molecular bond between a braze filler and a metallic material (such as titanium or gold) deposited on an outer surface of the optical element, and a second inter-molecular bond between the braze filler and an inner surface of the cannula.

In certain examples, the least one optical fiber included in the probe comprises a multi-core fiber or plurality of optical fibers.

In particular embodiments, a proximal end of the optical element is positioned within the cannula, and a distal end of the optical element protrudes beyond a distal end of the cannula. The optical element may protrude beyond the distal end of the cannula by a length in the range of 50-200 µm.

In certain variants of the disclosed laser probe, the lens may comprise a GRIN lens or a spherical lens, and the optical element may comprise an optically clear material. In certain examples, the optical element comprises sapphire or fused silica, and the cannula comprises stainless steel, nickel, titanium, nitinol, or platinum-iridium.

In certain embodiments of the disclosed laser probe, a diameter of the cannula is in the range of 200-700 µm, the optical element is cylindrically shaped, a diameter of the optical element is in the range of 200-700 µm, a length of the optical element is in the range of 200-700 µm, the lens is cylindrically shaped, a diameter of the lens is in the range of 200-700 µm, a length of the lens is in the range of 200 µm to 1.5 mm, and a thickness of the brazed joint is no greater than 50 µm.

In certain embodiments, the laser probe includes a body sized and shaped for grasping by a user, and the cannula is coupled to the body and is configured to be positioned within the eye of a patient.

Variants of the disclosed laser probe may include a proximal end of the optical element abutting the distal end of the lens. Additionally, a distal surface of the optical fiber may be pressed against a proximal surface of the lens, as a distal surface of the lens is pressed against a proximal surface of the optical element, such that the optical element functions as a mechanical stop with respect to the lens.

These and other aspects and uses will be described in the detailed description.

Figure 1:
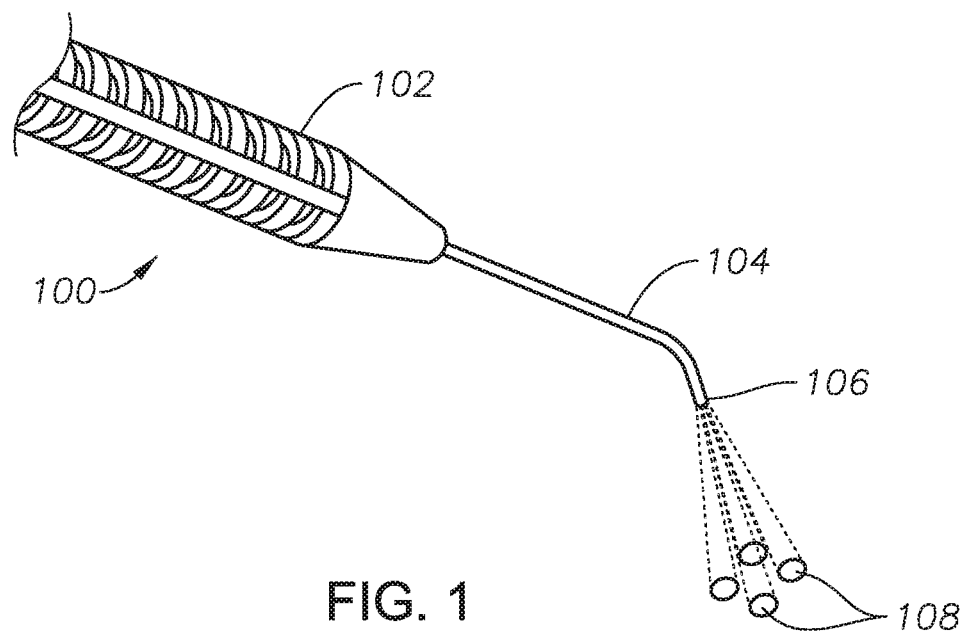
FIG. 1 illustrates an example multi-spot laser probe.

In the drawings, elements having the same designation have the same or similar functions. Those skilled in the art will appreciate that the figures are not necessarily to scale, and that several of the features may be exaggerated to more clearly illustrate various features. Those skilled in the art will also appreciate that the illustrated structures are exemplary, and do not limit the scope of the invention.

DETAILED DESCRIPTION

In the following description, details are set forth by way of example to facilitate discussion of the disclosed subject matter. It should be apparent to a person of ordinary skill in the field, however, that the disclosed implementations are exemplary and not exhaustive of all possible implementations. In some instances, features and procedures to well-known to those skilled in the art have not been described in order to avoid obscuring the disclosure. Unless defined otherwise, all technical and scientific terms used herein have the same meaning as commonly understood by one of ordinary skill in the art to which this disclosure belongs. Where a range of values is provided, it is understood that each intervening value between the upper and lower limit of that range and any other stated or intervening value in that stated range is included as an embodiment of the disclosure. The upper and lower limits of these smaller ranges are also included as an embodiment of the disclosure, subject to any specifically excluded limit in the stated range. Where the stated range includes both the upper and lower limits, ranges excluding either of those included limits are also included as an embodiment of the disclosure.

As noted above, in laser photocoagulation therapy a laser probe is used to cauterize the blood vessels at various laser burn spots across the retina. As the number of required laser photocoagulations for any one treatment of the retina may be quite large (exceeding 1000-1500 spots in some cases), a surgeon may use a multi-spot laser probe to deliver a plurality of photocoagulation beams simultaneously, thereby burning of multiple spots at a time and decreasing surgery time.

FIG. 1 illustrates an example of a multi-spot laser probe 100 which generates four laser spots 108 simultaneously. Probe 100 comprises a handle 102 sized and shaped for grasping by a user, such as an ophthalmic surgeon. Probe 100 further includes a cannula extending from handle 102 and 104 having a tip 106 at a distal end (which may or may not be curved as shown in various embodiments). Cannula 104 is adapted for insertion into a patient's eye, and may be cylindrically shaped. In various examples, cannula 104 may be made of stainless steel, titanium, nickel, nickel titanium (Nitinol), or platinum-iridium, and may be 23 Gauge, 25 Gauge, or 27 Gauge.

In operation, one or more laser beams from a laser source (not shown) are transmitted through one or more fibers within handle 102 and cannula 104 and delivered from the distal tip 106 onto a retina 108, producing spots 108. In some examples, probe 100 comprises multiple fibers or a multi-core fiber, each transmitting a laser beam which produces a separate one of spots 108. In other examples, a single fiber may transmit a laser beam which is split (e.g., using a spherical lens or gradient-index (GRIN) lens in probe 102) to produce each one of spots 108. Various multi-spot laser probe designs are described in U.S. Pat. No. 8,951,244, which is incorporated by reference herein in its entirety.

Figure 2:
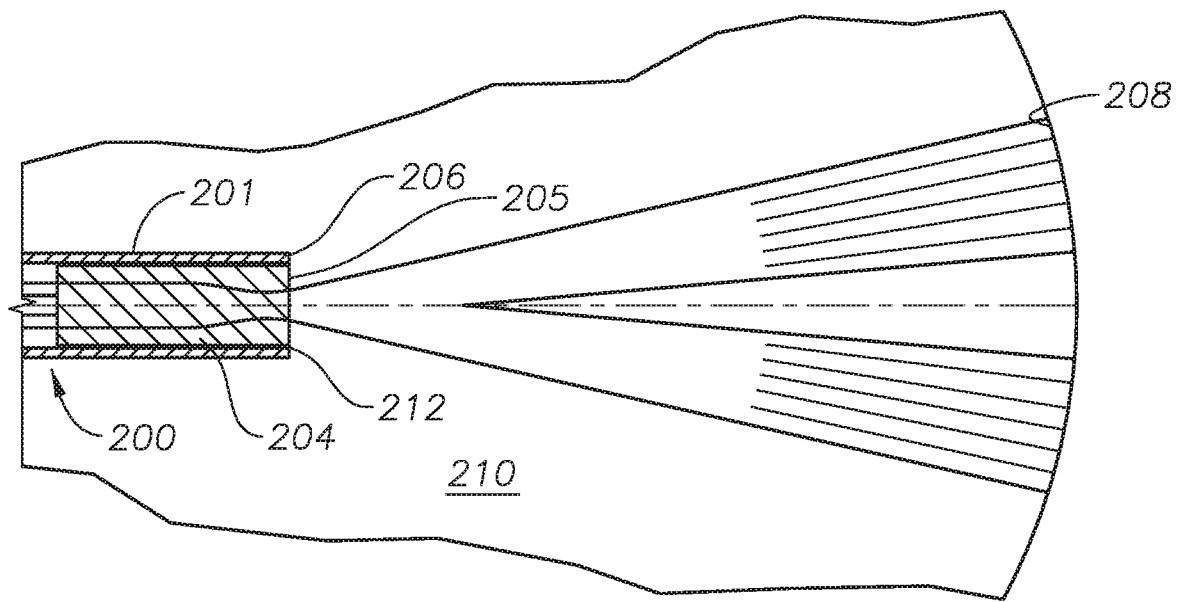
FIG. 2 illustrates aspects of a distal end of a conventional multi-spot laser probe.

FIG. 2 illustrates aspects of a conventional multi-spot laser probe. In this example, distal end 200 of a multi-spot laser probe includes a 2×2 fiber array 202 optically coupled to lens 204 located at the probe tip 206 within a cannula 201. In this design, lens 204 is the distalmost optical element of probe 200, and the distal surface of lens 204 is in physical contact with eye tissue 210 while probe 200 is inserted in an eye during a procedure. In operation, laser light is transmitted through fiber array 202, refracted by lens 204, and projected onto retina 208 as a plurality of laser spots.

In some surgical cases, blood or another foreign element may build up at probe tip 206, causing occlusion. For example, blood can occlude at the distal surface 205 of lens 204 during a surgical procedure. Blood occluded at distal surface 205 may char and absorb the laser energy, causing the temperature of lens 204 to rise. If this continues unabated, thermal runaway may occur and lens 204 may melt, resulting in failure of probe 200. In other instances, blood or another foreign element may seep into the space 212 between the outer surface of lens 204 and the inner surface of cannula 201. As in the prior example, such substances may absorb the laser energy, causing the temperature of lens 204 to rise. Left unabated, thermal runaway may occur and lens 204 may melt, resulting in failure of probe 200.

Embodiments of the present disclosure provide an improved multi-spot probe design that can resist thermal failure caused by blood and foreign substances during a procedure. Improved designs of a multi-spot probe may include a thermally robust optical element at the distalmost tip of the probe, attached to the cannula by a brazed joint. Probes built according to such a design isolate optical elements within the cannula, such as lenses, from occlusion of blood or other foreign substances encountered during a surgical procedure. Moreover, the brazed joint attaching the optically clear element to the cannula is impervious to penetration by foreign substances or blood. Accordingly, the lenses of such probes are not susceptible to thermal failure in the event of blood occlusion.

Figure 3A:
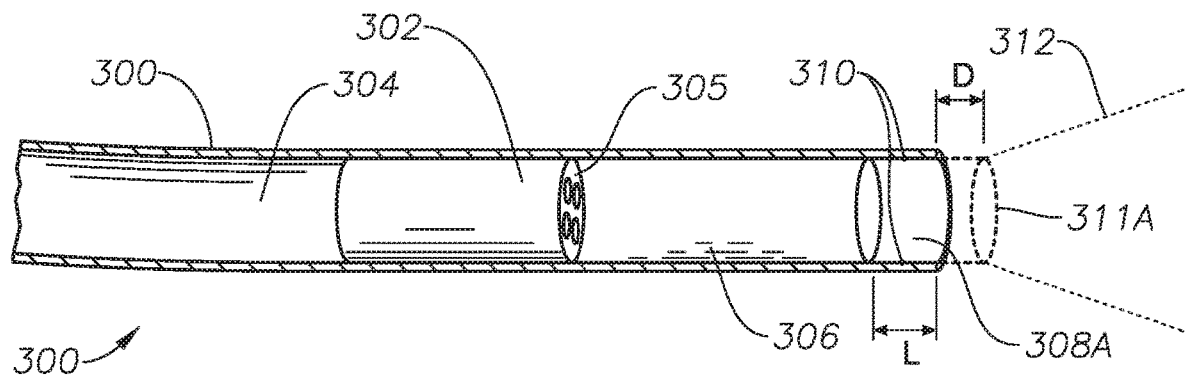
FIGS. 3A and 3B illustrate aspects of a distal end of a multi-spot laser probe, according to certain embodiments.
Figure 3B:
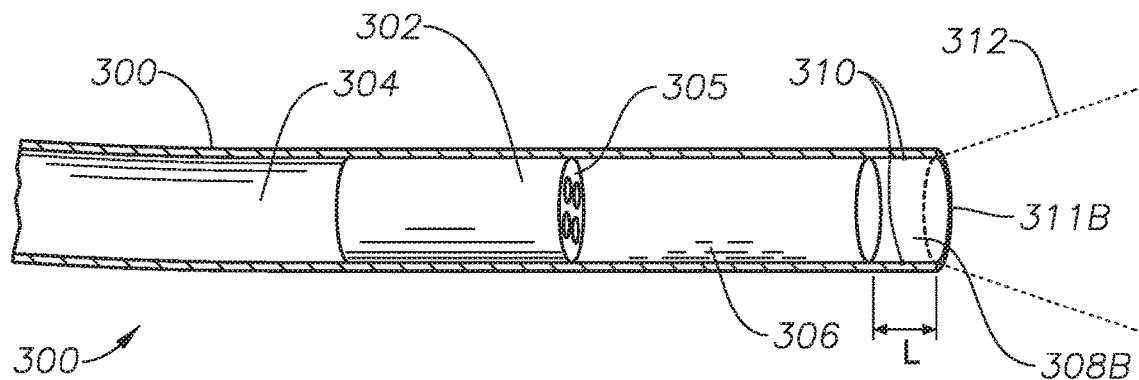

FIGS. 3A and 3B illustrate aspects of an improved multi-spot laser probe 102, according to certain embodiments. In particular, a distal tip 300 of a multi-spot laser probe 102 includes a cannula 301. Included within cannula 301 is multi-core optical fiber 302 surrounded by coating 304, as well as lens 306, and an optical element 308. In certain embodiments, a proximal end of optical element 308 abuts the distal end of the lens 306. In certain embodiments, the proximal end of lens 306 abuts the distal surface 305 of fiber 302. In certain examples, distal surface 305 of optical fiber 302 is pressed against a proximal surface of lens 306, and the distal surface of lens 306 is pressed against the proximal surface of optical element 308, such that the optical element functions as a mechanical stop with respect to lens 306.

Multi-spot laser light 312 is emitted from the distal surface of optical element 308. In operation, laser light received from a laser source (e.g., a laser engine, not shown) is transmitted through optical fiber 302, received and transmitted by lens 306, and is finally received and emitted as one or more focused laser beams 312 at the distal surface 311 of optical element 308.

Cannula 301 may be made of stainless steel, titanium, nickel, nickel titanium (Nitinol), platinum-iridium, or any other suitable material. Cannula 301 may be a 23 Gauge, 25 Gauge, 27 Gauge, or 29 Gauge cannula, or a larger or smaller gauge cannula. Cannula 301 may be shaped cylindrically in certain examples.

Multi-core optical fiber 302 may comprise glass or any suitable material for flexibly transmitting laser light. In the illustrated embodiments, optical fiber 302 includes four cores, though other embodiments may include fewer (e.g., one two, or three cores) or additional (e.g., five, six, or more cores) fiber cores. Although not illustrated, embodiments of the invention may include multiple multi-core fibers, such as two (or more) dual-core fibers, two (or more) tri-core fibers, or two (or more) quad-core fibers. Other embodiments may include multiple single-core fibers, such as two, three, or four, five, six, or more single-core fibers. In such embodiments, each core may transmit a beam of laser light which ultimately forms a single laser spot on the retina. In other embodiments, a laser beam transmitted by a single fiber may be split into multiple beams by an optical element (e.g., a diffractive beam splitter) within the probe or cannula. One skilled in the art will appreciate that these examples are provided to illustrate principles of the disclosure, but do not limit the scope of the invention.

Lens 306 may include one or more lenses comprising any suitable material, including visibly transparent glass or ceramics like fused silica, borosilicate, or sapphire. In certain examples, lens 306 comprises a single-element cylindrical GRIN rod lens which receives one or more laser beams from distal tip 305 of fiber 302 and relays the received laser beams toward optical element 308.

As noted above, given the high energy throughput (e.g., 1-3 Watts) and the confined space of distal tip 300, buildup of blood or other material on the distal surface of lens 306 during operation could cause light absorption and thermal-induced failure. Accordingly, optical element 308 is located distal to lens 306 and is designed to isolate and protect lens 306 (and other components in the probe) from exposure to foreign substances (e.g., tissue or blood in a surgical environment), overheating, and melting. Optical element 308 may comprise one or more elements made of an optically clear material with a high melting and high softening temperature, such as high softening point ceramics or glasses, and may be the distalmost optical element in the distal tip 300. In certain examples, optical element 308 comprises sapphire or fused silica.

In certain embodiments, optical element 308 comprises a single-element, optically clear window (e.g., made of sapphire, fused silica, or material with similar optical properties and softening/melting points) which may be cylindrically sized and shaped to fit within the distal end of the bore of cannula 300. In certain examples, optical element 308 may include flat proximal and distal surfaces to receive and emit laser light. In other examples, optical element 308 may include a flat proximal surface and curved distal surface, a curved proximal surface and flat distal surface, or curved proximal and distal surfaces.

Distal surface 311 of optical element 308 may extend beyond the distal end of cannula 301 in certain examples. To illustrate, FIG. 3A depicts an example in which distal surface 311A of optical element 308A protrudes beyond the distalmost tip of cannula 301 by a distance D. Distance D may be in the range of 50-200 µm in certain embodiments. In other embodiments, distance D may be less than 50 µm or greater than 200 µm. FIG. 3B illustrates an example in which distal surface 311B of optical element 308B does not protrude beyond the distal end of cannula 301. In this example, distal surface 311B is flush with the distalmost tip of cannula 301, so that it extends the full length of cannula 301 without extending beyond it.

As noted above, components distal tip 300 may be sized and shaped for ophthalmic applications, including insertion into an eye for a vitreoretinal surgery. Accordingly, in certain embodiments cannula 301 may have an inner diameter in the range of 200-700 µm, a cylindrically-shaped lens 302 may have a diameter in the range of 200-700 µm and a length in the range of 200 µm to 1.5 mm, and a cylindrically shaped optical element 308 may have a diameter in the range of 200-700 µm and length the range of 200-700 µm.

To provide a thermally robust, resilient, and well-sealed probe, optical element 308 may be coupled to cannula 301 by one or more brazed joints 310. During manufacture, a braze filler (or brazing compound) heated to a high temperature (near the softening or melting points of the materials being joined) can be used form inter-molecular bonds between the external surface of optical element 308 and the internal surface of cannula 300. The resulting brazed joint 310 may thus comprise a first inter-molecular bond between the braze filler and an outer surface of the optical element 308, and a second inter-molecular bond between the braze filler and an inner surface of the cannula. Braze filers useful with a sapphire or fused silica optical element 308 and a stainless steel, titanium, Nitinol) or platinum-iridium cannula 301 include gold and titanium, though the invention is not limited to these examples. A thickness of brazed joint 310 may, in some embodiments, be no greater than 50 µm.

In some embodiments, the outer surface of the optical element 308 may be partially or fully coated with a metallic material to facilitate formation of brazed joint 310. For example, the outer surface of a sapphire optical element 308 may be coated with a metallic material (such as titanium, gold, or other metals or alloys) via a sputtering process to form a metallic layer on the external surface of optical element 308 that is several atoms thick and bonds with optical element 310. In such examples, the metallic material and the braze filler may form an inter-molecular bond, constituting a portion of brazed joint 310. In certain embodiments, brazed joint 310 wraps circumferentially around cylindrical optical element 308 (and within cannula 301) and may extend across the all or a portion of length L corresponding to the overlap between optical element 308 and cannula 300.

Accordingly, brazed joint 310 may form a hermetic or fluid-tight seal between optical element 308 and cannula 301 protecting the internal components of distal tip 300 (including lens 306) from leaks or seepage which may occur in prior probe designs. Moreover, brazed joint 310 thermally insulates lens 310 in the case of occlusion at distal surface 311, avoiding overheating and thermal-induced failure that occurs in prior probe designs. As a result, combining an optical element 308 with a brazed joint 310 as discussed above provides a laser probe capable of high-power (e.g., 1-3 W) laser beam transmission with significantly reduced risk of overheating, meltdown, or other critical failures caused by light absorption at the probe tip (e.g., from blood occlusion). These and other benefits of the present invention will be apparent to those skilled in the art in view of the drawings and claims set forth herein.

The above disclosed subject matter is to be considered illustrative, and not restrictive, and the appended claims are intended to cover all such modifications, enhancements, and other implementations which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

The invention claimed is:
1. A laser probe, comprising:
  a cannula;
  at least one optical fiber positioned within the cannula;
  a lens positioned within the cannula distal to the fiber, the lens configured to receive a laser beam from the optical fiber at a proximal end of the lens and to transmit the laser beam towards a distal end of the lens;
  an optical element configured to receive the laser beam from the distal end of the lens and emit the laser beam from the probe;
  wherein the optical element is coupled to the cannula by a brazed joint;
  wherein the brazed joint forms a liquid-tight seal between the optical element and the cannula.

2. The laser probe of claim 1, wherein the brazed joint comprises:
   a first inter-molecular bond between a braze filler and an outer surface of the optical element; and
   a second inter-molecular bond between the braze filler and an inner surface of the cannula.

3. The laser probe of claim 1, wherein the brazed joint comprises:
   a first inter-molecular bond between a braze filler and a metallic material deposited on an outer surface of the optical element; and
   a second inter-molecular bond between the braze filler and an inner surface of the cannula.

4. The laser probe of claim 3, wherein the metallic material deposited on the outer surface of the optical element comprises at least one of titanium and gold.

5. The laser probe of claim 1, wherein the brazed joint forms a hermetic seal between the optical element and the cannula.

6. The laser probe of claim 1, wherein the at least one optical fiber comprises a multi-core fiber.

7. The laser probe of claim 1, wherein the at least one optical fiber comprises a plurality of optical fibers.

8. The laser probe of claim 1, wherein:
   a proximal end of the optical element is positioned within the cannula; and
   a distal end of the optical element is flush with a distal end of the cannula.

9. The laser probe of claim 1, wherein the lens comprises a GRIN (Gradient-index) lens or a spherical lens.

10. The laser probe of claim 1, wherein the optical element comprises an optically clear material.

11. The laser probe of claim 1, wherein the optical element comprises at least one of sapphire and fused silica.

12. The laser probe of claim 1, wherein the cannula comprises at least one of stainless steel, nickel, titanium, nitinol, and platinum-iridium.

13. The laser probe of claim 1, wherein:
   a diameter of the cannula is in the range of 200-700 μm;
   the optical element is cylindrically shaped;
   a diameter of the optical element is in the range of 200-700 μm;
   a length of the optical element is in the range of 200-700 μm;
   the lens is cylindrically shaped;
   a diameter of the lens is in the range of 200-700 μm;
   a length of the lens is in the range of 200 μm to 1.5 mm (millimeters); and
   a thickness of the brazed joint is no greater than 50 μm.

14. The laser probe of claim 1, further comprising:
   a body sized and shaped for grasping by a user; and
   wherein the cannula is coupled to the body and is configured to be positioned within an eye of a patient.

15. The laser probe of claim 1, wherein a proximal surface of the optical element abuts the distal surface of the lens.

16. The laser probe of claim 1, wherein:
   a distal surface of the optical fiber is pressed against a proximal surface of the lens; and
   a distal surface of the lens is pressed against a proximal surface of the optical element, such that the optical element functions as a mechanical stop with respect to the lens.

17. A laser probe, comprising:
   a cannula;
   at least one optical fiber positioned within the cannula;
   a lens positioned within the cannula distal to the fiber, the lens configured to receive a laser beam from the optical fiber at a proximal end of the lens and to transmit the laser beam towards a distal end of the lens;
   an optical element configured to receive the laser beam from the distal end of the lens and emit the laser beam from the probe;
   wherein the optical element is coupled to the cannula by a brazed joint;
   a proximal end of the optical element is positioned within the cannula; and
   a distal end of the optical element protrudes beyond a distal end of the cannula.

18. The laser probe of claim 17, wherein the distal end of the optical element protrudes beyond the distal end of the cannula by a length in the range of 50-200 μm (micrometers).

19. A laser probe, comprising:
   a body sized and shaped for grasping by a user;
   a cannula coupled to the body and configured to be positioned within an eye of a patient;
   a multi-core fiber positioned within the cannula;
   a GRIN lens positioned within the cannula distal to the multi-core fiber, the GRIN lens configured to receive a laser beam from the multi-core fiber at a proximal end of the lens and to transmit the laser beam towards a distal end of the lens;
   an optical element comprising an optically clear window configured to receive the laser beam from the distal end of the lens and emit the laser beam from the probe, wherein a proximal end of the optical element is positioned within the cannula, and a distal end of the optical element protrudes beyond a distal end of the cannula; and
   a brazed joint coupling the optical element to the cannula, the brazed joint forming at least one of a hermetic seal and a liquid-tight seal between the optical element and the cannula.

* * * * *